(12) United States Patent
Shiomi et al.

(10) Patent No.: US 7,214,287 B2
(45) Date of Patent: May 8, 2007

(54) PROCESS FOR CONTINUOUSLY MAKING DISPOSABLE WEARING ARTICLES

(75) Inventors: Akihisa Shiomi, Kagawa-ken (JP); Akihide Ninomiya, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 137 days.

(21) Appl. No.: 10/995,895

(22) Filed: Nov. 24, 2004

(65) Prior Publication Data

US 2005/0072512 A1    Apr. 7, 2005

Related U.S. Application Data

(63) Continuation of application No. PCT/JP03/01007, filed on Aug. 6, 2003.

(30) Foreign Application Priority Data

Aug. 6, 2002   (JP)  ............................. 2002-228522
Aug. 1, 2003   (JP)  ............................. 2003-205464

(51) Int. Cl.
*B29C 65/48*   (2006.01)
*B29C 43/46*   (2006.01)
*B32B 37/22*   (2006.01)
*B29C 43/56*   (2006.01)
*B29C 65/74*   (2006.01)

(52) U.S. Cl. ...................... 156/269; 156/249; 156/302; 156/516; 156/538

(58) Field of Classification Search .................. 83/156, 83/703, 436.3–436.9, 436.1; 156/249, 257
See application file for complete search history.

(56) References Cited

U.S. PATENT DOCUMENTS 5,151,092 A  *  9/1992  Buell et al. .............. 604/385.3

FOREIGN PATENT DOCUMENTS

| EP | 1 132 325 A2 | 9/2001 |
| JP | 61-287645 | 12/1986 |
| JP | 02-291857 | 12/1990 |
| JP | 2003-079661 | 3/2003 |
| WO | 95 35079 | 12/1995 |

OTHER PUBLICATIONS

International Search Report for PCT/JP03/10007, mailed from the Japanese Patent Office on Sep. 24, 2003.

* cited by examiner

*Primary Examiner*—Melvin Mayes
*Assistant Examiner*—Sonya Mazumdar
(74) *Attorney, Agent, or Firm*—Lowe Hauptman & Berner LLP

(57) ABSTRACT

In a process for continuously making disposable wearing articles, a first web which will be finally cut into a series of sheet members that are contiguous to one another in a transverse direction, and that define an outer surface of the article, is continuously fed in a first machine direction. A second web having a Ω-shaped cross-section forming individual adhesive taper strips is fed in a second machine direction orthogonal to the first machine direction. The second web is periodically cut in a second cross direction orthogonal to the second machine direction to obtain composites. After the composite is fed to and attached to the first web, the first web is cut together with the composite so as to bisect the length of the composite.

12 Claims, 13 Drawing Sheets

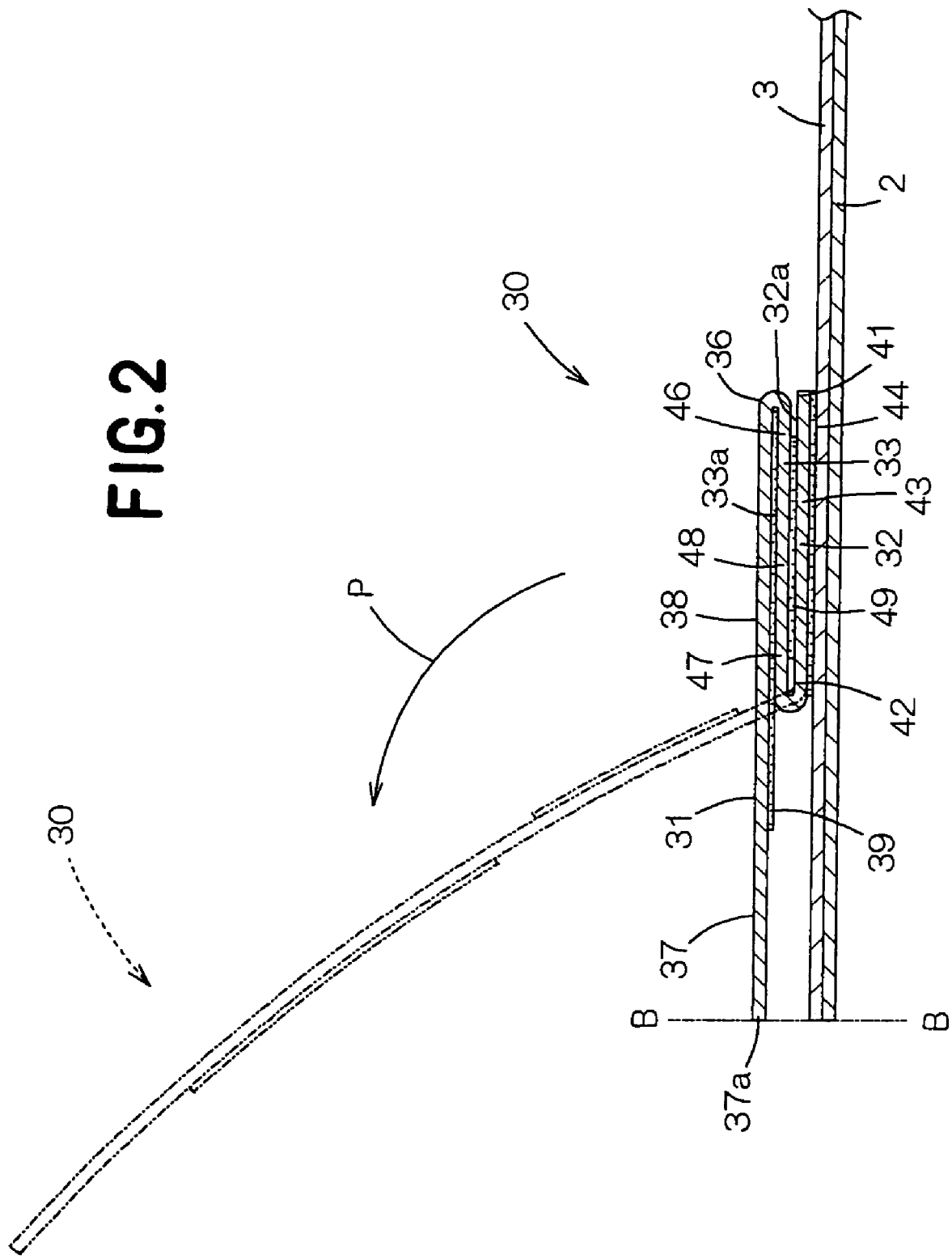

//PROCESS FOR CONTINUOUSLY MAKING DISPOSABLE WEARING ARTICLES

BACKGROUND OF THE INVENTION

The present invention relates to a process for continuously making disposable wearing articles such as disposable diapers, disposable training pants or disposable pants.

EP 1 132 325 A2 discloses an apparatus adapted to attach adhesive tape strips to a continuous web comprising a series of diapers being still contiguous to one another in its one direction intermittently in one direction of the continuous web. In the case of this apparatus, continuous web comprising a series of adhesive tape strips being still contiguous to one another is introduced between a cutter roll and an anvil roll and thereby cut into the individual adhesive tape strips. These adhesive tape strips are fed and attached to the continuous web of disposable diapers running in one direction. A feed speed of the continuous web of the adhesive tape strips is substantially equal to a rotational speed of the anvil roll and these speeds are lower than a running speed of the continuous web of disposable diapers. The anvil roll lies immediately below the continuous web of disposable diapers and rotates to the running direction of this continuous web. The adhesive tape strips run in the same direction as the continuous web of disposable diapers runs and successively bonded to the continuous web of disposable diapers.

Japanese Patent Application Publication No. 1986-287645A discloses a tape applicator adapted to feed tape strips each having a predetermined length in a web running direction and to attach the tape strips to the running web. The tape strip is fed in a direction orthogonal to the web running direction and then fed in the web running direction before attached to the web. This applicator is adapted to attach the tape strips to the web so that a plurality of the tape strips may be spaced apart from one another parallel to one another. The speed at which the tape strips are fed in the web running direction is equal to the running speed of the web.

In the above-cited references, the adhesive tape strips are fed in the same direction as the web runs and attached to the web. When it is desired to attach the adhesive tape strips to the web of disposable diapers contiguous to one another at positions corresponding to both side edges of the individual diapers according to the above-cited known art, the web running direction should be orthogonal to the transverse direction of the individual diapers. In other words, the above-cited Publication disclose none of processes adapted to attach the adhesive tape strips to the side edges of the individual diapers at a high efficiency.

SUMMARY OF THE INVENTION

It is an object of the present invention to provide a process for continuously making disposable wearing articles improved so that the adhesive tape strips can be efficiently attached to the web comprising a plurality of disposable wearing articles contiguous to one another in a transverse direction of the articles so that each pair of the adhesive tape strips can be positioned on both side edges of the individual article.

In accordance with the present invention, there is provided a process for continuously making disposable wearing articles, the article having a longitudinal direction and a transverse direction orthogonal to the longitudinal direction so as to define a waist-circumferential direction of the article, the article comprising an inner surface facing a wearer's body, an outer surface facing a wearer's garment and a pair of tape strips each having a longitudinal direction and a transverse direction and attached to the outer surface of the article at side edge portions thereof opposed to each other, respectively, so that the longitudinal direction of the tape strip is in conformity with the transverse direction of the article, one of the tape strips being folded in a generally Z-shape while the other of the tape strips being folded in a generally inverted Z-shape, the pair of the tape strips comprising a top tape section, a bottom tape section and an intermediate tape section connecting the top tape section to the bottom tape section so as to define the Z- or inverted Z-shape, the bottom tape section being configured to be unreleasably attached to the outer surface of the article and provided on a lower surface of the bottom tape section with an adhesive zone, the top tape section being configured to be releasably attached to the outer surface of the article and provided on a lower surface of the top tape section with a releasably attaching zone and each of the tape strips being attached to the outer surface of the article at the adhesive zone.

The process according to the present invention comprises the steps of:

(1) continuously feeding a first web comprising a plurality of sheet members being contiguous to one another in the transverse direction, each forming at least a part of the outer surface of the article, in a first machine direction;

(2) continuously feeding a second web comprising a plurality of composites of the tape strips being contiguous to one another in the transverse direction of the tape strips, in a second machine direction wherein each of the composites comprises a pair of the tape strips folded in the Z- and inverted Z-shape, respectively, either tape sections of the top tape sections and the bottom tape sections in the composite being contiguous at respective ends thereof and a remainder of the tape sections being spaced apart from each other so as to have a vertically depressed Ω-shape;

(3) introducing the second web fed in the second machine direction between an upper tool roll rotating in the second machine direction about an axis extending in a second cross direction orthogonal to the second machine direction and a lower tool roll extending parallel to the upper tool roll and rotating in the second machine direction so that the upper surfaces of the top tape sections in the composite are kept in close contact with a peripheral surface of the lower tool roll and cutting the second web periodically in the second cross direction to obtain the composites arranged intermittently in a circumferential direction of the lower tool roll;

(4) compressively squeezing the bottom tape sections of the composite kept on the peripheral surface of the lower tool roll between the lower tool roll and pressure means adapted to move close to the lower tool roll periodically as the lower tool roll rotates and therefore the lower surfaces of the bottom tape sections in the composite are opposed to the first web running in the first machine direction and securing the bottom tape sections of the composite to the first web at the adhesive zones so that the composite extends across a boundary between each pair of the adjacent sheet members of the first web and evenly extend on adjacent sheet members of the first web; and (5) cutting the first web together with the composites in a first cross direction orthogonal to the first machine direction so that the dimension of the composites in the first machine direction is generally bisected, respectively, to obtain the individual sheet members provided on the side edge potions opposed to each other in the first machine direction with the pair of tape strips one of which is folded in the Z-shape and the other is folded in the inverted Z-shape.

The present invention includes the following embodiments.

The article is a disposable diaper, disposable training pants or disposable pants, the sheet member is configured to be the outer surface of the article in a front or rear waist region and the first web comprises a plurality of the sheet members connected to one another at side edges thereof in the front or rear waist region.

The lower tool roll is adapted to rotate in the second machine direction at a constant rotational speed and a ratio between the rotational speed per minute of the lower tool roll and a running speed per minute of the first web in the first machine direction is in a range of 1:2 to 1:40.

The pressure means comprise a pair of hammer rolls extending parallel to each other and adapted to rotate in the first machine direction.

The releasably attaching zone includes an adhesive agent coated on the tape strip to be releasably attached to a predetermined portion of the outer surface.

The releasably attaching zone includes a hook member provided on the tape strip to be releasably attached to a predetermined portion of the outer surface.

The middle tape section is releasably attached to the releasably attaching zone of the top tape section of the tape strip folded in the Z- or inverted Z-shape.

At least the middle tape section among the top tape section, the bottom tape section and the middle tape section is made of a nonwoven fabric which is releasably engageable with a hook member of a mechanical fastener provided on the top tape section.

BRIEF DESCRIPTION OF THE DRAWINGS

FIG. 2 is a sectional view taken along a line II—II in FIG. 1;

DETAILED DESCRIPTION OF THE PREFERRED EMBODIMENTS

The process according to the present invention for continuously making disposable wearing articles will be more fully understood from the description given hereunder with reference to the accompanying drawings.

Figure 1:
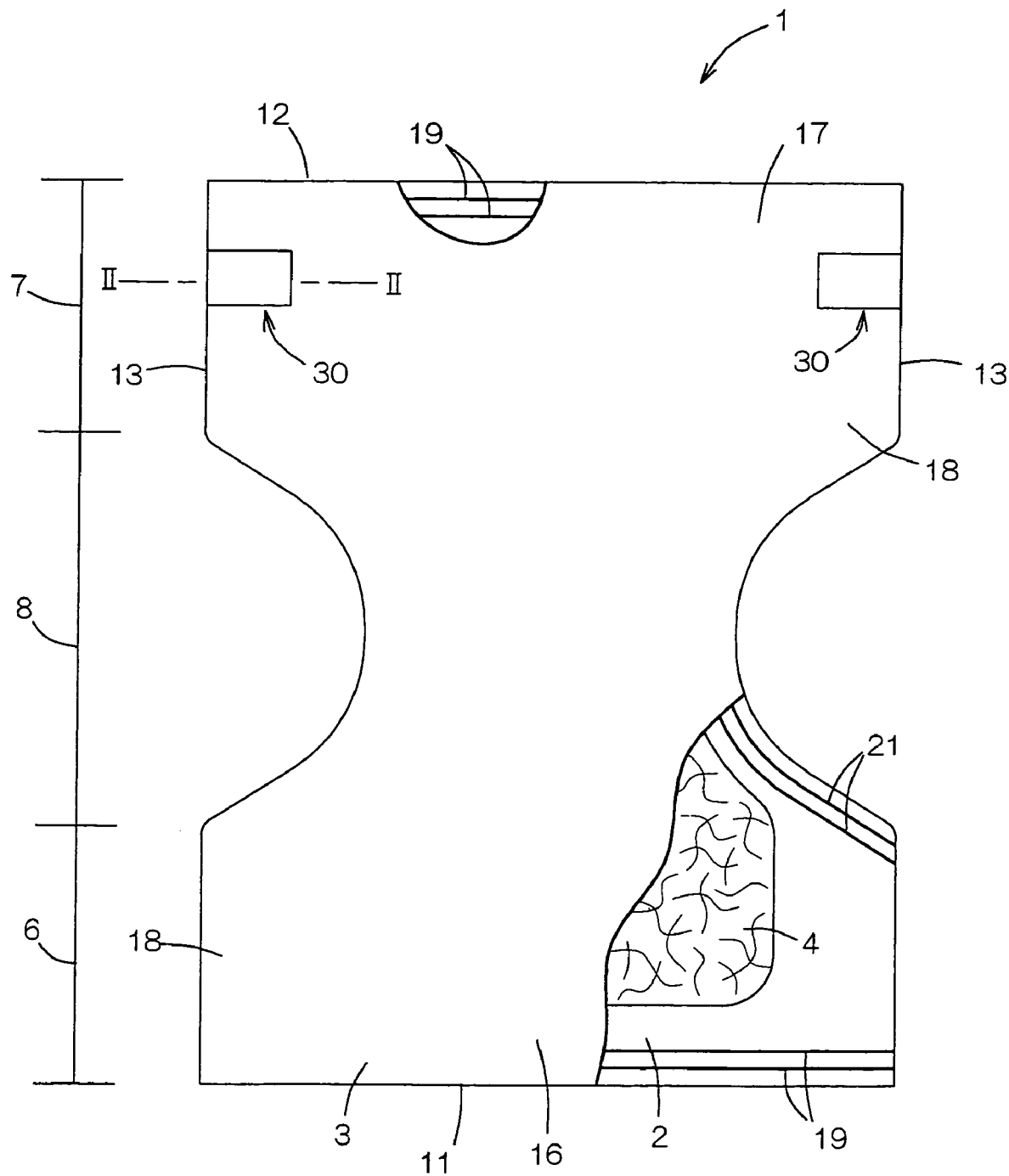
FIG. 1 is a partially cutaway plan view showing an example of the disposable diaper made by the process according to the invention.

FIG. 1 is a partially cutaway plan view showing an example of the disposable diaper 1 made by the process according to the invention and FIG. 2 is a sectional view taken along a line II—II in FIG. 1. The diaper 1 comprises a liquid-pervious topsheet 2 defining a surface facing a wearer's body, a liquid-impervious backsheet 3 defining a surface facing the wearer's garment and a liquid-absorbent core 4 interposed between these two sheets 2, 3. The diaper 1 is illustrated in FIG. 1 as the backsheet 3 overlies the topsheet 2. The diaper 1 is contoured by front and rear ends 11, 12 extending parallel to each other transversely of the diaper 1 (i.e., in a transverse direction as viewed in FIG. 1) and a pair of side edges 13 extending in a longitudinal direction orthogonal to the transverse direction. As viewed in the longitudinal direction, a front waist region 6 is formed aside toward the front end 11, a rear waist region 7 is formed aside toward the rear end 12 and a crotch region 8 extends between these two waist regions 6, 7. In the crotch region 8, the side edges 13 curve inward to describe circular arcs. The top- and backsheets 2, 3 are overlaid and joined together outward beyond a peripheral edge of the core 4 by means of a hot melt adhesive agent (not shown) so as to form a front flap 16, a rear flap 17 and a pair of side flaps 18. In the front and rear flaps 16, 17, waist-surrounding elastic members 19 are secured in a stretched state to the inner surface of at least one of the top- and backsheet 2, 3. In the respective side flaps 18, thigh-surrounding elastic members 21 are secured in a stretched state to the inner surface of at least one of the top- and backsheets 2, 3 along the side edges 13 thereof. A pair of tape fasteners 30 comprising strips of pressure-sensitive adhesive tape are attached to the backsheet 3 in the rear waist region 7 in the vicinity of the respective side edges 13. The tape fasteners 30 are respectively folded so that these tape fasteners 30 can be unfolded outward beyond the respective side edges 13.

As will be apparent from FIG. 2, each of the tape fasteners 30 comprises a top tape section 31, a bottom tape section 32 and an intermediate tape section 33 interposed between top and bottom tape sections 31, 32. The tape section 31 has an inner end portion 36 lying inside the diaper 1, an outer end portion 37 lying outside the diaper 1 and an intermediate portion 38 extending between these inner and outer end portions 36, 37. The inner end and intermediate portions 36, 38 have lower surfaces thereof coated with a first adhesive agent 39 having mild pressure-sensitive properties. The outer end portion 37 extends outward of the diaper 1 beyond the intermediate tape section 33 and forms a finger-grip. The bottom tape section 32 has an inner end portion 41, an outer end portion 42 and intermediate portion 43. These portions 41 through 43 have respective lower surfaces coated with a second adhesive agent 44 having high adhesion properties. The intermediate tape section 33 has an inner end portion 46, an outer end one 47 and an intermediate section 48. These portions 46 through 48 have respective lower surfaces coated with a third adhesive agent 49 having mild pressure-sensitive properties. The top tape section 31 is releasably attached for a temporarily fixing purpose to the upper surface 33a of the intermediate tape section 33 over a mild adhesive zone coated with the first adhesive agent 39 on the inner end portion 36 and the intermediate portion 38. The bottom tape section 32 is secured to an outer surface (an upper surface shown in FIG. 2) of the backsheet 3 over a high adhesive zone coated with the second adhesive agent 44. The intermediate tape section 33, except its inner end portion 46 being contiguous to the top tape section 31 and the outer end portion 47 being contiguous to the bottom tape section 32, is releasably attached to the upper surface 32a of the bottom tape section 32. The tape fastener 30 comprising the top tape section 31, the intermediate tape section 33 and the bottom tape section 32 contiguous to one another in this manner is folded in a Z-shape. The tape fastener 30 is unfolded as indicated by imaginary lines as the outer end portion 37 of the top tape section 31 is held between the fingers and pulled outward of the diaper 1 in a direction indicated by an arrow P and thereby the respective sections releasably attached to one another is easily peeled off from one another. In order to ensure that the bottom tape section 32 and the intermediate tape section 33 are easily released from the first and third adhesive agents 39, 49, these tape sections 32, 33 may be previously coated on predetermined zones with a release agent such as a silicone oil.

Figure 3A:
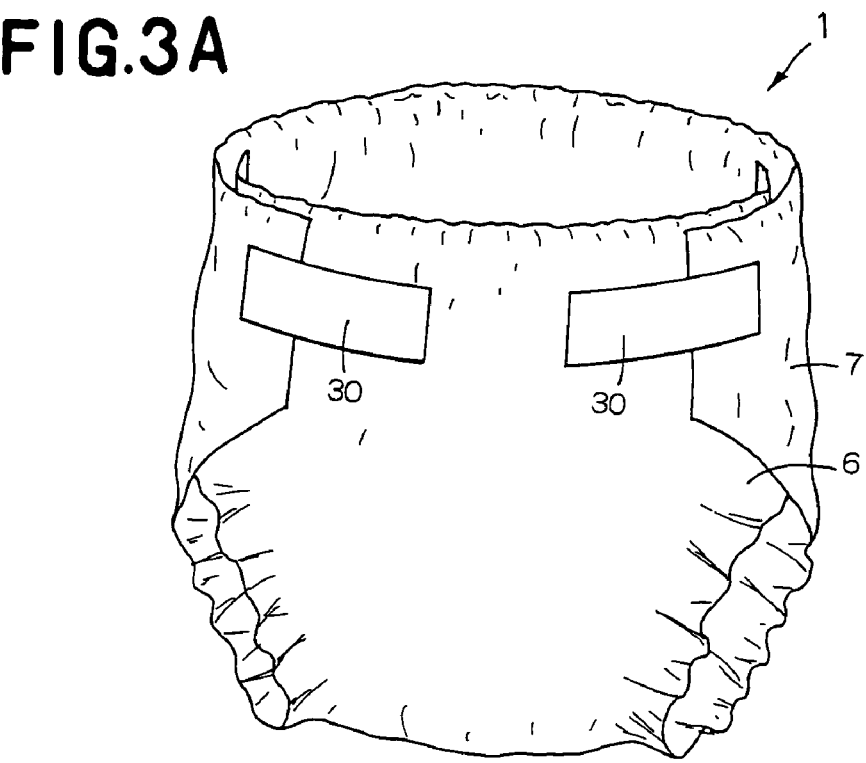
FIG. 3A illustrates a manner of utilizing tape fasteners and FIG. 3B illustrates another manner of utilizing the tape fasteners.
Figure 3B:
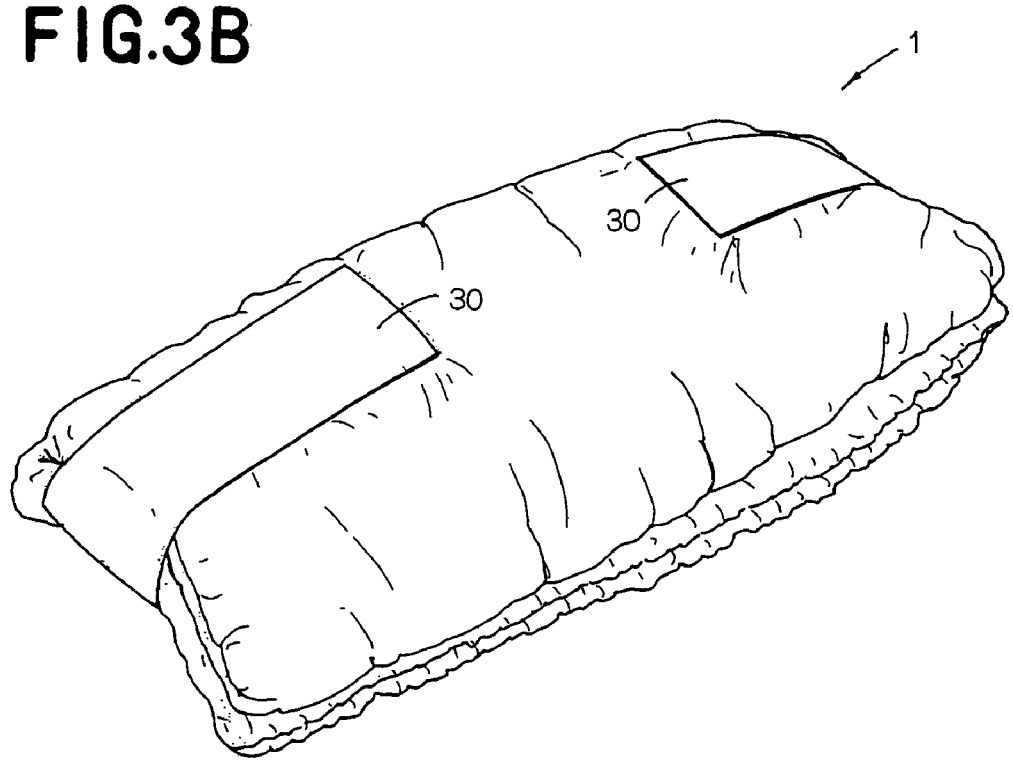

FIG. 3A illustrates the diaper 1 put one the wearer's body with the tape fasteners 30 unfolded from the rear waist region 7 are releasably attached to the front waist region 6 by means of the first adhesive agent 39 and FIG. 3B illustrates the diaper 1 used and rolled up and held by the tape fasteners 30 in a rolled up state. In this manner, the portion of the top tape section 31 coated with the first adhesive agent 39 acts as a zone attaching releasably to the outer surface or the inner surface of the diaper 1, and, therefore, the tape fasteners 30 can be used as adhesive tape means both for putting the diaper 1 on the wearer's body and for disposal of the diaper 1 after use. Even if the diaper 1 is of pull-on type, i.e. pants type, the tape fasteners 30 may be used to tighten the wearer's waist region or to hold the used diaper in a rolled up state for disposal (see FIGS. 12 and 13).

Figure 4:
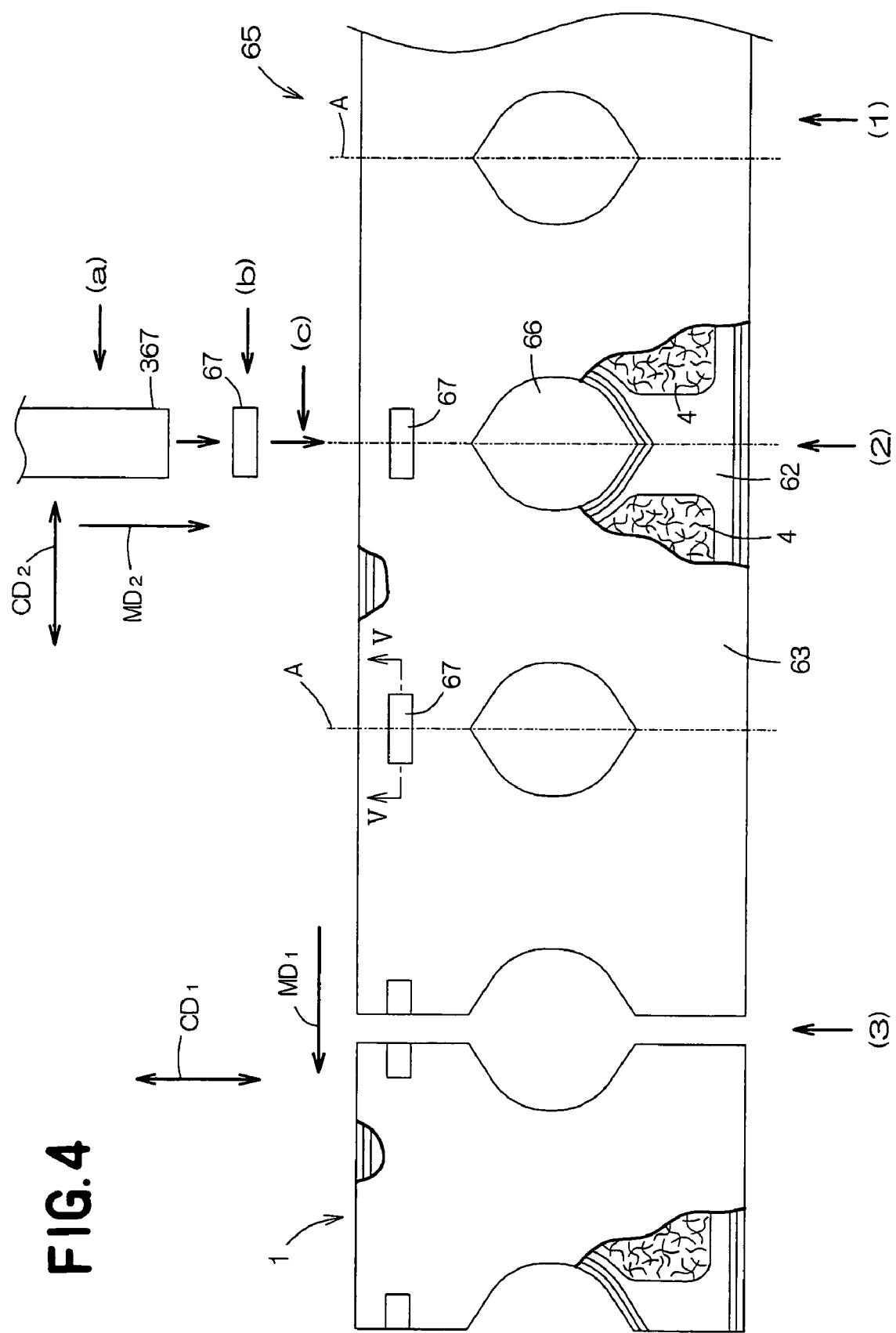
FIG. 4 is a diagram partially illustrating the process for making the diaper.

FIG. 4 is a diagram partially illustrating the process according to the invention for continuously making the diaper 1. In a series of steps (1) through (3) illustrated in a lower part of this diagram, a direction in which the process goes on from the right to the left is a first machine direction $MD_1$ and a direction orthogonal to this direction $MD_1$ is a first cross direction $CD_1$. In the step (1), a first composite web 65 comprising a continuous liquid-pervious web 62 configured to become the topsheet 2 of the diaper 1, a continuous liquid-impervious web 63 overlying the web 62 and configured to become the backsheet 3 and cores 4 intermittently interposed between these webs 62, 63 at predetermined intervals in the first machine direction $MD_1$ is continuously fed in the first machine direction $MD_1$. These webs 62, 63 are overlaid and joined together outward beyond peripheral edges of the respective cores 4 by means of hot melt adhesive agent (not shown). A dimension of the first composite web 65 as measured in the first cross direction $CD_1$ corresponds to a dimension of the diaper 1 as measured in its longitudinal direction and imaginary lines A extending in the first cross direction $CD_1$ correspond to the transversely opposite side edges 13 of the respective diapers 1. In the web 62, a plurality of the topsheets 2 of the individual diapers 1 are connected to one another at the side edges 13. Similarly in the web 63, a plurality of the backsheets 3 of the individual diapers 1 are connected to one another at the side edges 13. The cores 4 are placed between respective pairs of the adjacent imaginary lines A and generally circular portions are cut out from the webs 62, 63 placed upon each other in a generally middle zone as viewed in the transverse direction of these webs 62, 63 to form openings 66. Each of these cut out portions is symmetric about each of the imaginary lines A.

In the step (2), composites 67 each configured to form the individual tape fastener 30 are fed from a series of steps (a) through (c) illustrated in an upper part of FIG. 4 and attached to the first composite web 65 so that the composites 67 may extend across the respective imaginary lines A so as to be bisected by the respective imaginary lines A. The composite 67 includes a pair of the tape fasteners 30 arranged so as to be symmetric about a vertical line B—B passing through outermost ends 37a of the respective top tape sections 37 and having the respective top tape sections 37 being contiguous at respective outermost ends thereof and the respective bottom tape sections 32 spaced apart from each other in the longitudinal direction of the bottom tape section 32 as will be understood from FIG. 2. Thus the composite 67 has a vertically compressed Ω-shape in its side view.

In the step (3), the first composite web 65 is successively cut together with the composites 67 along the imaginary lines A to obtain the individual diapers 1 shown in FIG. 1. Peripheral edges of the respective openings 66 formed in the first composite web 65 define the side edges 13 of the respective diapers 1 describing the generally circular arcs in the crotch regions 8.

In the series of steps (a) through (c) illustrated in the upper part of FIG. 4, the composites 67 are prepared. In the step (a), a continuous second composite web 367 configured to be cut into the individual composites 67 is fed in a second machine direction $MD_2$ orthogonal to the first machine direction $MD_1$. In the step (b), the second composite web 367 is successively cut in a transverse direction of the second composite web 367, i.e., a second cross direction $CD_2$ orthogonal to the second machine direction $MD_2$ into the individual composite 67. In the step (c), the composites 67 are successively fed onto the first composite web 65. The second composite web 367 comprises a plurality of the composites 67 which are contiguous to one another as viewed in a transverse direction thereof.

Figure 5:
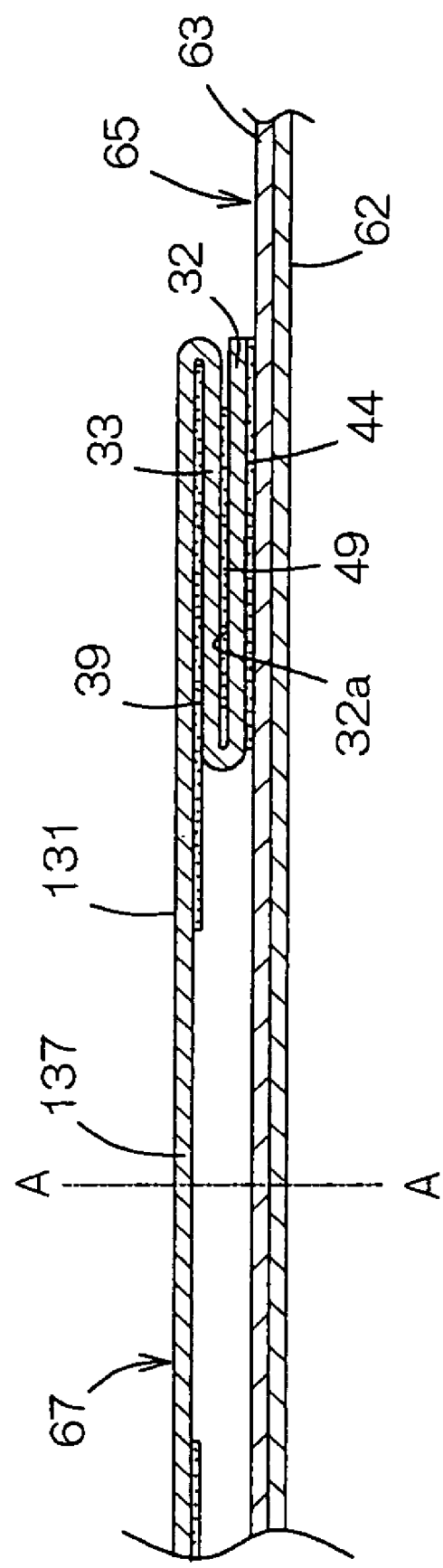
FIG. 5 is a sectional view taken along a line V—V in FIG. 4.

FIG. 5 is a sectional view of the first composite web 65 including the composites 67 shown in FIG. 4 as taken along a line V—V in FIG. 4. The composite 67 attached to the first composite web 65 is substantially symmetric about the imaginary line A and the left half of the composite 67 is not illustrated in FIG. 5. The composite 67 comprises a first tape section 131 extending across the imaginary line A in the first machine direction $MD_1$, the bottom tape sections 32 lying on both sides of the imaginary line A and secured to the liquid-impervious web 63 by means of the second adhesive agent 44 and the intermediate tape sections 33 lying on both sides of the imaginary line A and releasably attached to the upper surfaces 32a of the respective bottom tape sections 32 by means of the third adhesive agent 49. The first tape section 131 is releasably attached to the intermediate tape sections 33 from above by means of the first adhesive agent 39 and is provided in the vicinity of the imaginary line A with a middle zone 137 not coated with the first adhesive agent 39. As the first composite web 65 and the composites 67 are successively cut along the imaginary lines A, the individual diapers 1 each provided with a pair of the tape fasteners 30 are obtained, the liquid-pervious web 62 and the liquid-impervious web 63 become the topsheet 2 and the backsheet 3, respectively. In each half of the composite 67 bisected along the imaginary line A, the first tape section 131, the first adhesive agent 39 and the middle zone 137 respectively become the top tape section 31, the first adhesive agent 39 and the outer end portion 37 serving as the finger-grip of the tape fastener 30 shown in FIG. 2. Similarly, the bottom tape section 32 and the second adhesive agent 44 of the composite 67 respectively become the bottom tape section 32 and the second adhesive agent 44 of the diaper 1 while the intermediate tape section 33 and the third adhesive agent 49 of the composite 67 respectively become the intermediate tape section 33 and the third adhesive agent 49 of the diaper 1. As best seen in FIG. 5, of two tape fasteners 30 obtained from the single composite 67, the tape fastener 30 lying on the right side of the imaginary line A is folded in a generally Z-shape and the tape fastener 30 lying on the left side of the imaginary line A is folded in a generally inverted Z-shape. In FIG. 1, the tape fastener 30 folded in a Z-shape lies on the left side of the diaper 1 and the tape fastener 30 folded in an inverted Z-shape lies on the right side of the diaper 1.

The process according to the invention for continuously making the individual diapers 1 in the manner as has been described above has advantageous effects that the first composite web 65 comprising a plurality of the diapers 1 contiguous to one another is cut together with the composites 67 attached to the first composite web 65 and therefore the number of steps for cutting the stock tape material to obtain the tape fastener 30 can be reduced by one and labor as well as time required to attach the tape fastener 30 to the diaper 1 can be also reduced by half as compared to the case in which the individual tape fasteners 30 are prepared and then attached this to the diaper 1 one by one.

Figure 6:
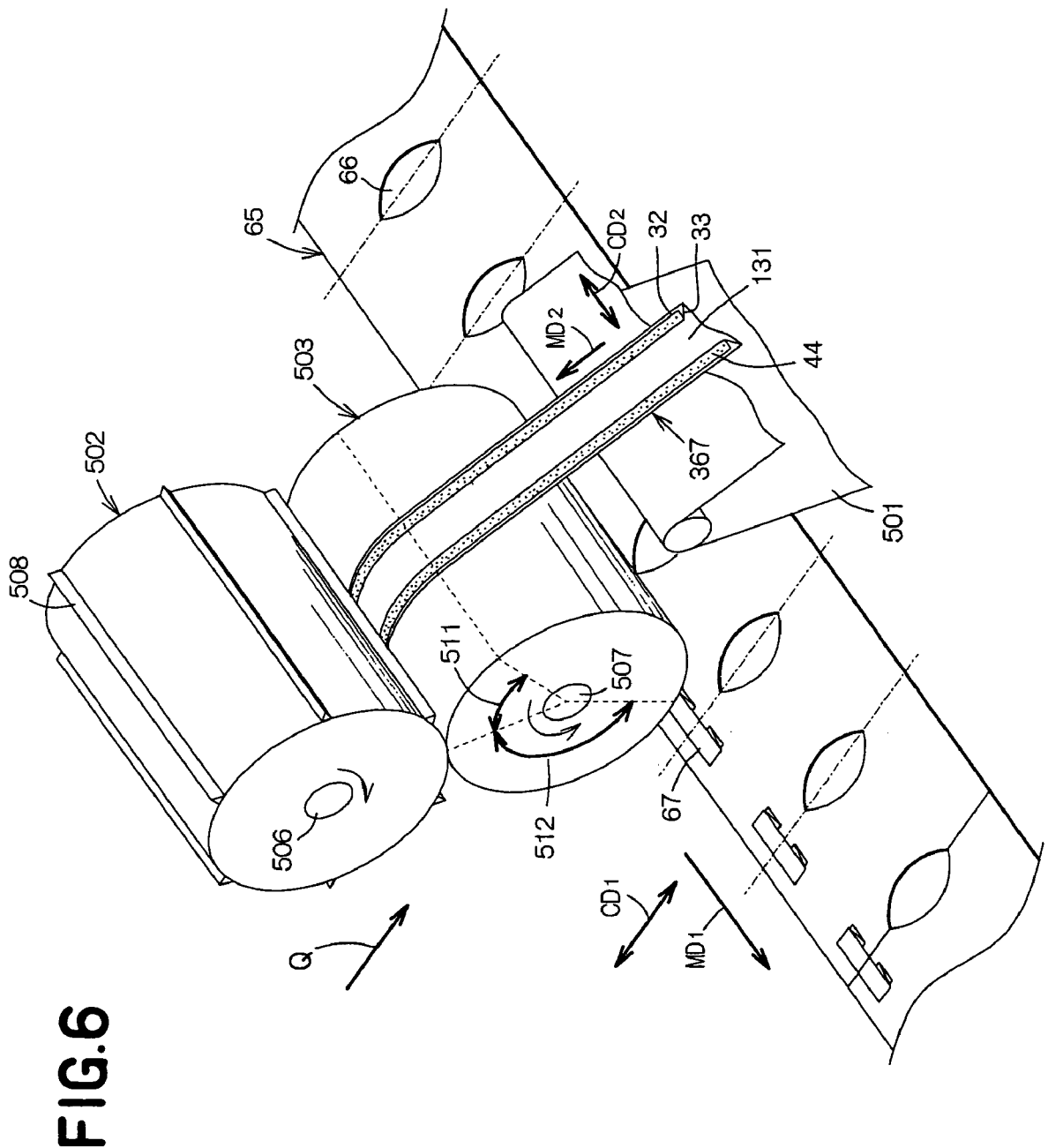
FIG. 6 is a diagram illustrating a part of FIG. 4 more in detail.

FIG. 6 is a perspective view showing a part of the device serving to feed the composite 67 of the tape fasteners 30 onto the first composite web 65 shown in FIG. 4. Referring to FIG. 6, the first composite web 65 runs in the first machine direction $MD_1$ at a constant speed. The second composite web 367 is conveyed by an endless belt 501 running in the second machine direction $MD_2$ orthogonal to the first machine direction $MD_1$ onto a peripheral surface of a lower tool roll 503 and then guided between an upper tool roll 502 and the lower tool roll 503. The endless belt 501 is under a vacuum suction which enables the second composite web 367 to be kept in close contact with the belt 501 while the second composite web 367 is conveyed. The endless belt 501 maybe replaced by nip rolls (not shown) adapted to hold the second composite web 367 held between rolls while the second composite web 367 is conveyed.

The upper tool roll 502 and the lower tool roll 503 extend parallel to each other and continuously rotate about axes 506, 507, respectively, extending in the second cross direction $CD_2$ orthogonal to the second machine direction $MD_2$. The upper tool roll 502 is provided on its peripheral surface with a plurality of blades 508 extending parallel to the axis 506 at regular intervals in the circumferential direction of the upper tool roll 502 and the lower tool roll 503 is provided on its peripheral surface with a plurality of vacuum suction holes (not shown). The vacuum suction from the interior of the lower tool roll 503 is relatively weak as the peripheral surface of the lower tool roll 503 passes over a first zone 511 and relatively strong as the peripheral surface of the lower tool roll 503 passes over a second zone 512. The top tape section 131 of the second composite web 367 is kept in close contact with the peripheral surface of the lower tool roll 503 in the first zone 511 due to the relatively weak vacuum suction.

The second composite web 367 runs in the second machine direction $MD_2$ at a same speed as that of the endless belt 501 and the peripheral surface of the lower tool roll 503 in the first zone 511 rotates with a slippage relative to the second composite web 367 supported thereon. As a result, the second composite web 367 is prevented from running further forward and thereby the length of the second composite web 367 in the second machine direction $MD_2$ is kept constant on the peripheral surface of the lower tool roll 503. A predetermined dimension of the second composite web 367 as measured in the second machine direction $MD_2$ is cut off by the blades 508 arranged at regular intervals on the peripheral surface of the upper tool roll 502 as every predetermined time has elapsed and thereby the composite 67 is obtained. After the composite 67 has been cut off, the second composite web 367 supported on the lower tool roll 503 is allowed to run forward by the dimension which has been cut off. Upon completion of this cutting off operation, the lower tool roll 503 rotates from the first zone 511 to the second zone 512 and the composite 67 now closely contacted to the peripheral surface of the lower tool roll 503 under the relatively strong vacuum suction runs further forward in the second machine direction $MD_2$ until the bottom tape section 32 of the composite 67 coated with the second adhesive agent 44 faces downward. The lower tool roll 503 lies immediately above the first composite web 65, so the composite 67 closely contacted to the lower tool roll 503 comes close to the first composite web 65 most as the composite 67 comes to its lowest position in the vertical direction.

Figure 7:
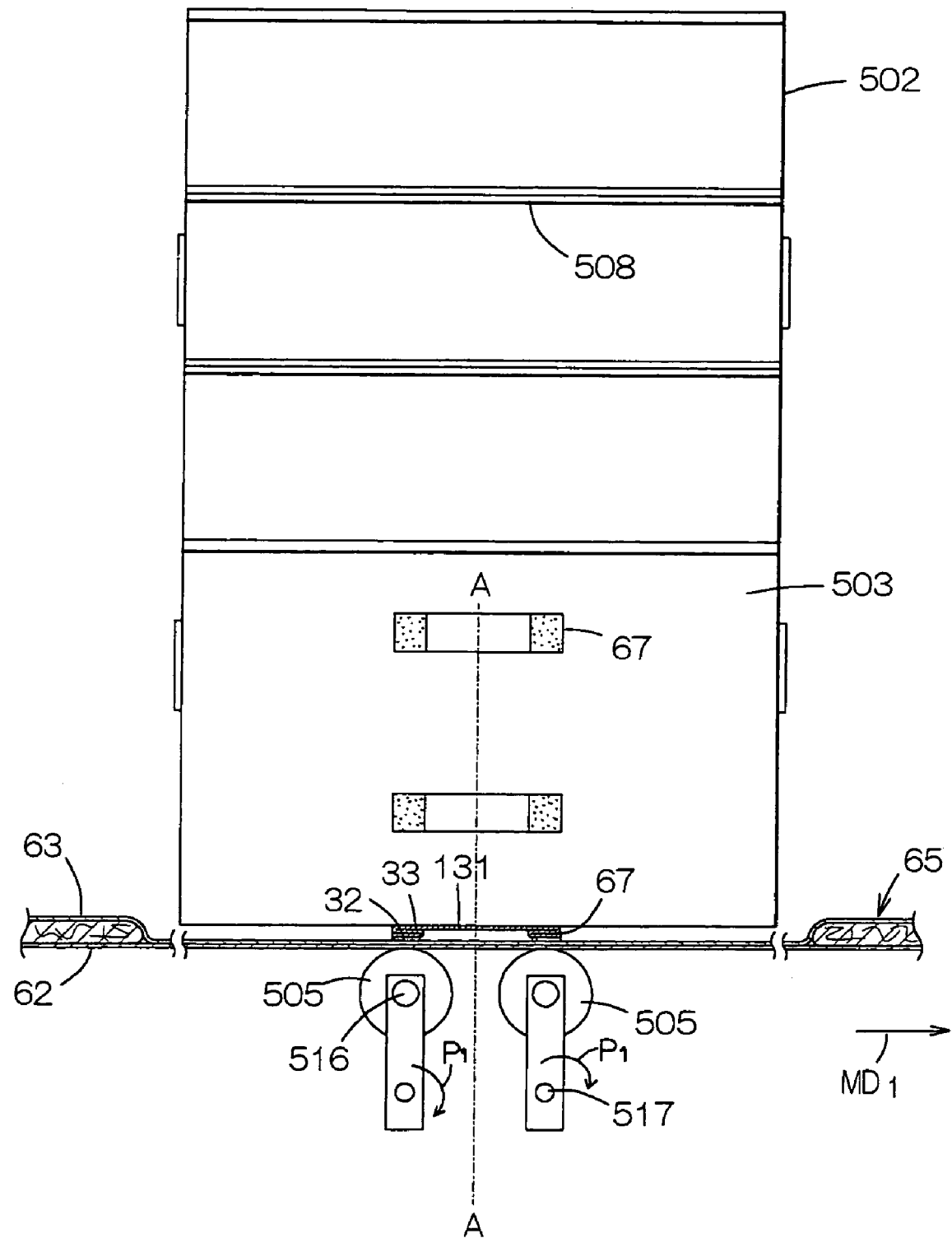
FIG. 7 is a diagram illustrating the devices in FIG. 6 as viewed in a direction indicated by an arrow Q.
Figure 8:
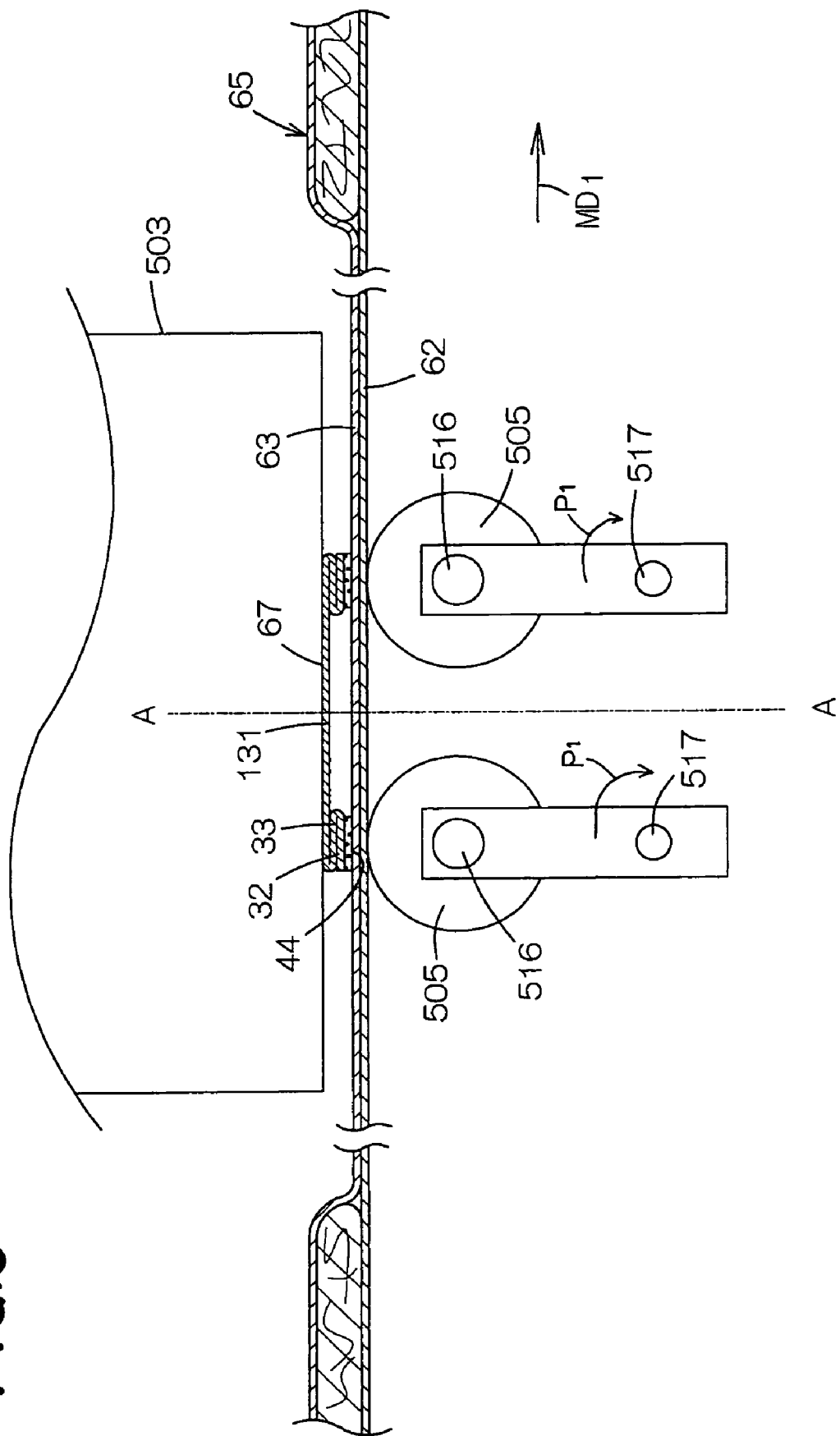
FIG. 8 is a scale-enlarged diagram illustrating a part of FIG. 7.

FIG. 7 is a diagram illustrating the devices in FIG. 6 as viewed in a direction indicated by an arrow Q and FIG. 8 is a scale-enlarged diagram illustrating a part of FIG. 7. The lower tool roll 503 lies immediately above the first composite web 65 running in the first machine direction $MD_1$ and a pair of hammer rolls 505 lie immediately below the first composite web 65. These hammer rolls 505 continuously rotate in a direction indicated by an arrow $P_1$, i.e., in the first machine direction $MD_1$ about axes 517 extending in the first cross direction $CD_1$ orthogonal to the first machine direction $MD_1$ (see FIG. 6), respectively, while the respective hammer rolls 505 rotate about axes 516 extending parallel to the axes 517, respectively.

The lower tool roll 503 rotates in synchronization with running of the first composite web 65 as well as rotation of the hammer rolls 505 about axes 517 so that the imaginary line A (see FIG. 4) of the first composite web 65 comes to a position at which the composite 67 is bisected along this imaginary line A in the first machine direction $MD_1$ as the composite 67 of the tape fasteners 30 closely contacted to the lower tool roll 503 comes to a position immediately above the first composite web 65 at which the composite 67 is opposed to the first composite web 65. Simultaneously, the pair of hammer rolls 505 respectively come to positions immediately below the lower tool roll 503 at which these hammer rolls 505 face upward in the vertical direction. A clearance between the hammer rolls 505 facing upward in the vertical direction and the lower tool roll 503 is adjusted so that, in the vicinity of the imaginary lines A of the first composite web 65, this first composite web 65 comprising the liquid-pervious web 62 and the liquid-impervious web 63 placed upon each other may be effectively joined to the composite 67 comprising the top tape section 13, the bottom tape sections 32 and the intermediate tape sections 33 as the web 65 and the composite 67 are compressively squeezed between the hammer rolls 505 and the lower tool roll 503. More specifically, the bottom tape sections 32 of the composite 67 are secured to the first composite web 65 by means of the second adhesive agent 44 as the first composite web 65 and the composite 67 are squeezed between the lower tool roll 503 and the hammer rolls 505. Upon completion of such securing, the hammer rolls 505 rotate about the axes 517 in the first machine direction $MD_1$ and come away from the first composite web 65. The first composite web 65 having the composites 67 secured thereto is fed in the first machine direction $MD_1$ and, in this course, cut along the respective imaginary lines A to obtain the individual diapers 1.

According to the process for continuously making the diaper 1 in which the tape fasteners 30 are attached to the respective diapers 1 via the steps as illustrated by FIGS. 4 through 8, the composite 67 configured to be the pair of fasteners 30 usually has a width in a range of 10 to 40 mm. The lower tool roll 503 adapted to support a plurality of the composites 67 arranged intermittently on its peripheral surface and closely contacted thereto under the effect of vacuum suction may have a relatively small diameter, e.g., in the order of 200 mm to support six composites 67 equally spaced apart from one another in the circumferential direction of the lower tool roll 503 and more or less contacted to the peripheral surface. With the lower tool roll 503 dimensioned in this order, the peripheral surface of the roll 503 rotates in the second machine direction $MD_2$ by a distance corresponding to ⅙ of its circumferential length, i.e., approximately by 105 mm as the first composite web 65 is advanced in the first machine direction $MD_1$ by a distance corresponding to the single diaper 1. Taking account of the fact that a distance between each pair of the adjacent imaginary lines A corresponding to a width of the single diaper 1 is usually in a range of 200 to 500 mm, a travel distance ratio between the peripheral surface of the lower tool roll 503 having the composites 67 supported thereon and the first composite web 65 is 105:200 to 105:500, i.e., approximately 1:2 to 1:5. By reducing the diameter of the lower tool roll 503 in this manner so that the circumferential travel distance of the lower tool roll 503 may be smaller than the travel distance of the first composite web 65 per a single diaper 1, the position of composite 67 relative to the first composite web 65 can be stabilized in the first cross direction $CD_1$ corresponding to the longitudinal direction of the diaper 1. So far as the travel distance of the peripheral surface is sufficient small, it is not likely that the position of the composite 67 in the first cross direction $CD_1$ might significantly shift from the predetermined position even if a certain degree of fluctuation occurs in the speed of the lower tool roll 503. To minimize the position shift of the composite 67 in the first cross direction $CD_1$ both in the case of the diaper 1 for infants and in the case of the diaper 1 for adults, a ratio of travel distance between the peripheral surface of the lower tool roll 503 and the first composite web 65 is preferably 1:2 to 1:40. This ratio corresponds to the ratio between a rotational speed of the lower tool roll 503 per minute and a running speed of the first composite web 65 per minute.

In general, higher the rotational speeds of the upper and lower tool rolls 502, 503, higher the possibility that the various components such as the blades 508 are readily damaged, the composites 67 are apt to fly off as these composites 67 are cut off from the second composite web 367 and, in consequence, the position of the composite 67 on the peripheral surface of the lower tool roll 503 become unstable. According to the present invention, however, the rotational speeds of the upper and lower tool rolls 502, 503 are sufficiently reduced to alleviate damages of the blades 508 and the other components and to stabilize the position of the composite 67 on the peripheral surface of the lower tool roll 503.

The hammer rolls 505 serve as pressure means to join the composite 67 to the first composite web 65. Without departing from the scope of the invention, these hammer rolls 505 may be replaced by any other suitable means adapted to periodically move close to the lower tool roll 503 and join the composite 67 to the first composite web 65 as the composite 67 supported on the lower tool roll 503 is opposed to the first composite web 65.

Figure 9:
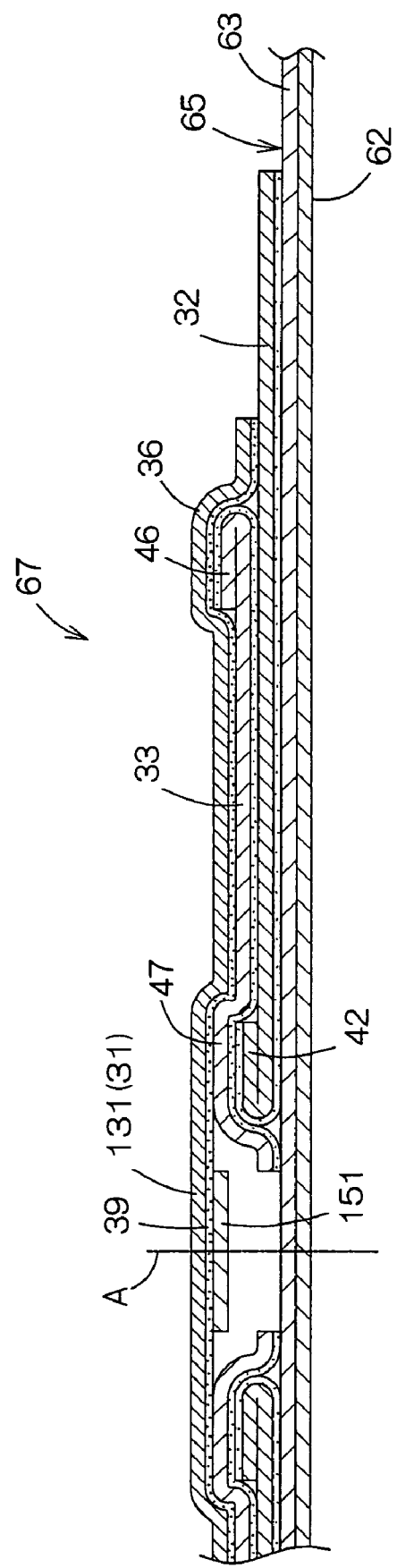
FIG. 9 is a view similar to FIG. 5 showing another embodiment of the tape fastener shown in FIG. 2.

FIG. 9 is a view similar to FIG. 5 showing the composite 67 configured to be the tape fastener 30 differing from that shown in FIG. 2. It is possible to adopt the composite 67 as shown in FIG. 9 without departing from the scope of the present invention. The tape fastener 30 obtained from the composite 67 is distinguished from that of FIG. 2 in that the top tape section 31 obtained from the top tape section 131, the bottom tape section 32 and the intermediate tape section 33 are independent from one another and connected at the end portions thereof which are associated with one another. More specifically, the inner end portion 46 is folded upward and connected in a folded state to the inner end portion 36 of the top tape section 31. The outer end portion 42 of the bottom tape section 32 is folded upward and connected in such a folded state to the outer end portion 47 of the intermediate tape section 33. Referring to FIG. 9, the top tape section 131 extends beyond the imaginary line A and coated on its entire lower surface with the first adhesive agent 39 having mild pressure-sensitive properties. The adhesive agent 39 is covered with a plastic film strip 151 in the vicinity of the imaginary line A. The top tape section 131 is cut along the imaginary line A together with the plastic film strip 151 to obtain the top tape section 31 shown in FIG. 2 and a zone defined by the plastic film strip 151 forms the finger-grip.

Figure 10:
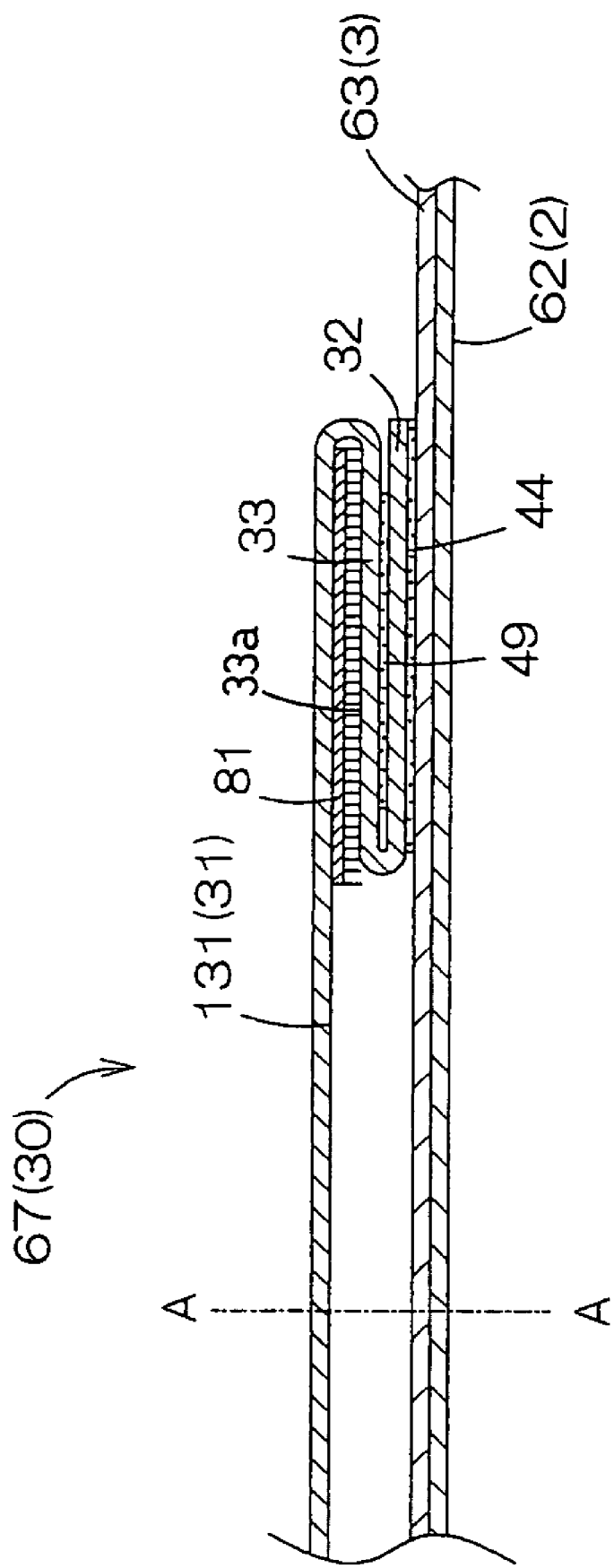
FIG. 10 is a view similar to FIG. 5 showing an embodiment of the composite (i.e., the tape fastener)

FIG. 10 is a view similar to FIG. 5 showing a preferred example of the composite 67 configured to become the tape fastener 30. In the case of the tape fastener 30 obtained from this composite 67, the top tape section 31 obtained from the first tape section 131 is provided on the lower surface thereof with an anchoring zone, i.e. a releasably attaching zone, defined by a hook member 81 to be used a part of so-called mechanical fastener. Of the top tape section 31, the bottom tape section 32 and the intermediate tape section 33, at least the intermediate tape section 33 or its lower surface 33a facing the hook member 81 is made of a sheet material with which the hook member 81 releasably engages, for example, nonwoven fabric having a plurality of loops. The bottom tape section 32 is unreleasably bonded to the liquid-impervious web 63 configured to form the backsheet 3 by means of the second pressure-sensitive adhesive 44. The intermediate tape section 33 is releasably attached to the bottom tape section 32 so as to be easily peeled off from the bottom tape section 32. With the diaper 1 having the tape fastener 30 obtained from such a composite 67, the sheet material having a plurality of loops defines a target zone onto which the hook member 81 is to be engaged when the diaper 1 is put on the wearer's body. If the backsheet 3 of the diaper 1 is made of a sheet material such as nonwoven fabric having a plurality of loops, the backsheet as a whole can be utilized as the target zone.

Figure 11:
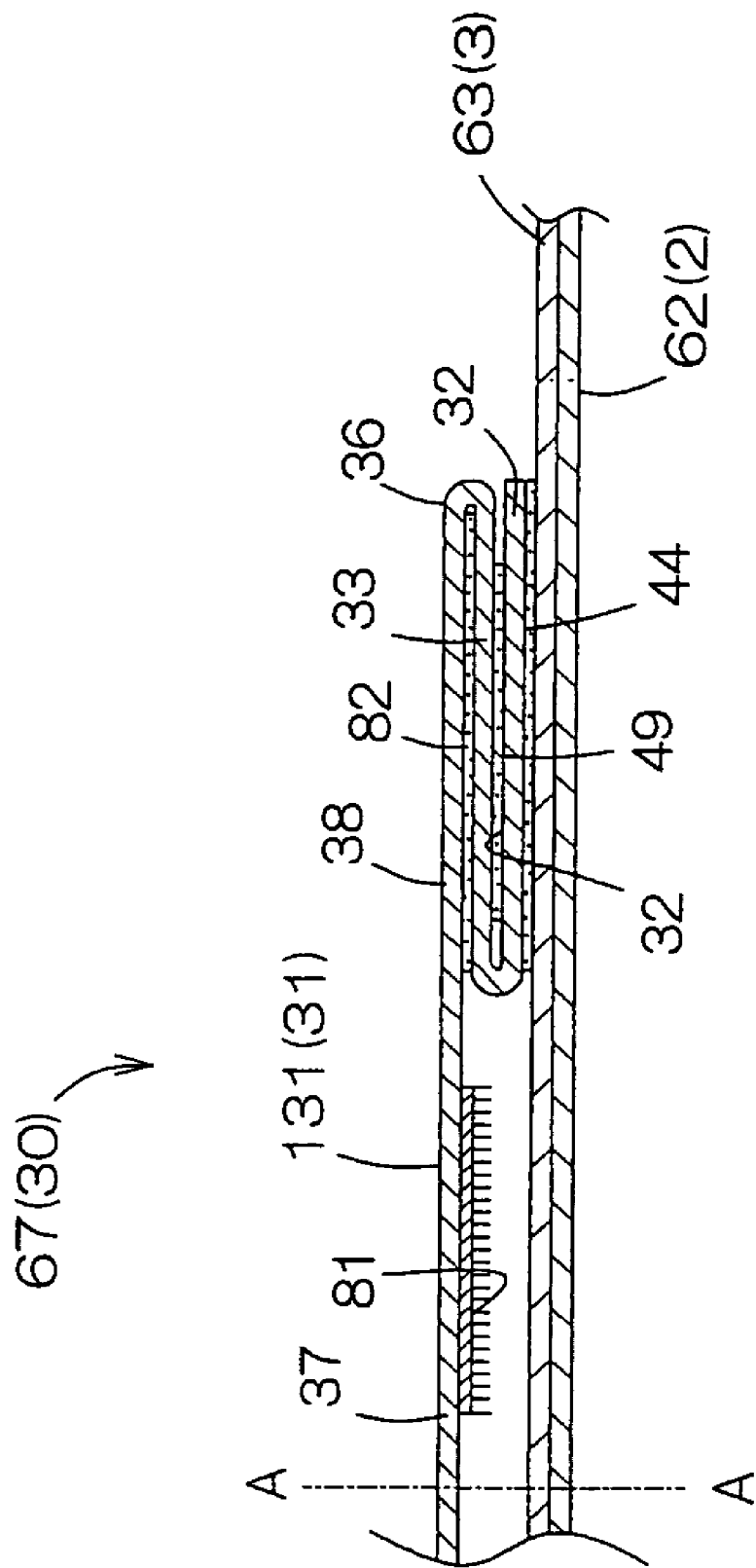
FIG. 11 is a view similar to FIG. 10 showing another embodiment of the composite (i.e., the tape fastener)

FIG. 11 is a view similar to FIG. 10 showing another preferred example of the composite 67 configured to become the tape fastener 30. The tape fastener 30 obtained from this composite 67 is characterized in that the outer end portion 37 of the top tape section 31 extending aside from the intermediate tape section 33 toward the imaginary line A—A is provided on its lower surface with the hook member 81 defining the anchoring zone. The intermediate portion 38 of the top tape section 31 is releasably attached to the intermediate tape section 33 by means of a mild pressure-sensitive adhesive 82. The intermediate tape section 33 is releasably attached to the bottom tape section 32 which is, in turn, unreleasably bonded to the liquid-impervious web 63 which is configured to form the backsheet 3. In the tape fastener 3 of this example, the hook member 81 is utilized in the same manner as in the example depicted in FIG. 9. The liquid-impervious web 63 or its outer surface can be made of such a sheet material as a nonwoven fabric engageable with the hook member 81. In the case that the hook member 81 engages with the liquid-impervious web 63 during the process of the present invention, the adhesive 82 can be deleted if requested.

Figure 12:
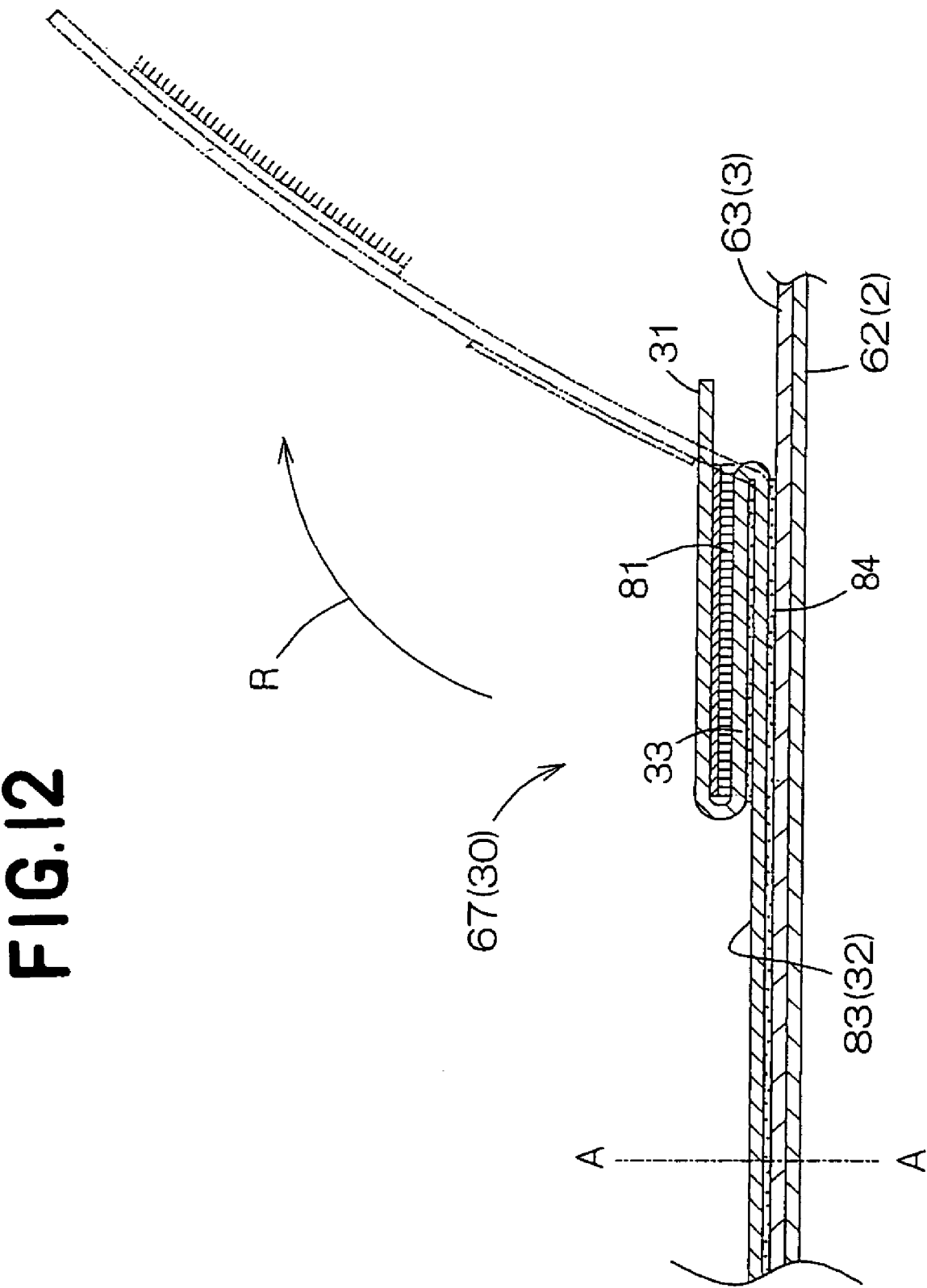
FIG. 12 is a view similar to FIG. 10 showing still another embodiment of the composite (i.e., the tape fastener)

FIG. 12 is a view similar to FIG. 10 showing still another preferred example of the composite 67. This composite 67 is distinguished from that depicted in FIG. 10 in that the bottom sheet 83 configured to become the bottom tape section 32 of the tape fastener 30 extends beyond the imaginary line A—A to the tape fastener 30 to the located on the left side of FIG. 12 (not shown). The top tape section 31 and the intermediate tape section 32 are folded together so as to be unfolded in the direction indicated by an arrow R. The top tape section 31 is provided on its lower surface with the hook member 81 defining the anchoring zone, i.e. the releasably attaching zone, and this hook member 81 is releasably attached to the intermediate tape section 33 having a plurality of loops. The intermediate tape section 33 is releasably attached for a temporarily fixing purpose to the bottom sheet 83, i.e., the bottom tape section 32. The bottom sheet 83 is unreleasably bonded over its substantially full length to the liquid-impervious web 63 which is configured to become the backsheet 3 by means of a pressure-sensitive adhesive 84 having high bonding strength. The top tape section 31 may extend beyond the middle tape section 33 toward the transversely middle point of the diaper 1. In this tape section 31 a portion of the hook member 81 which extends beyond the middle tape section 33 can engage with the outer surface of the liquid-impervious web 63 made of a nonwoven fabric.

Figure 13:
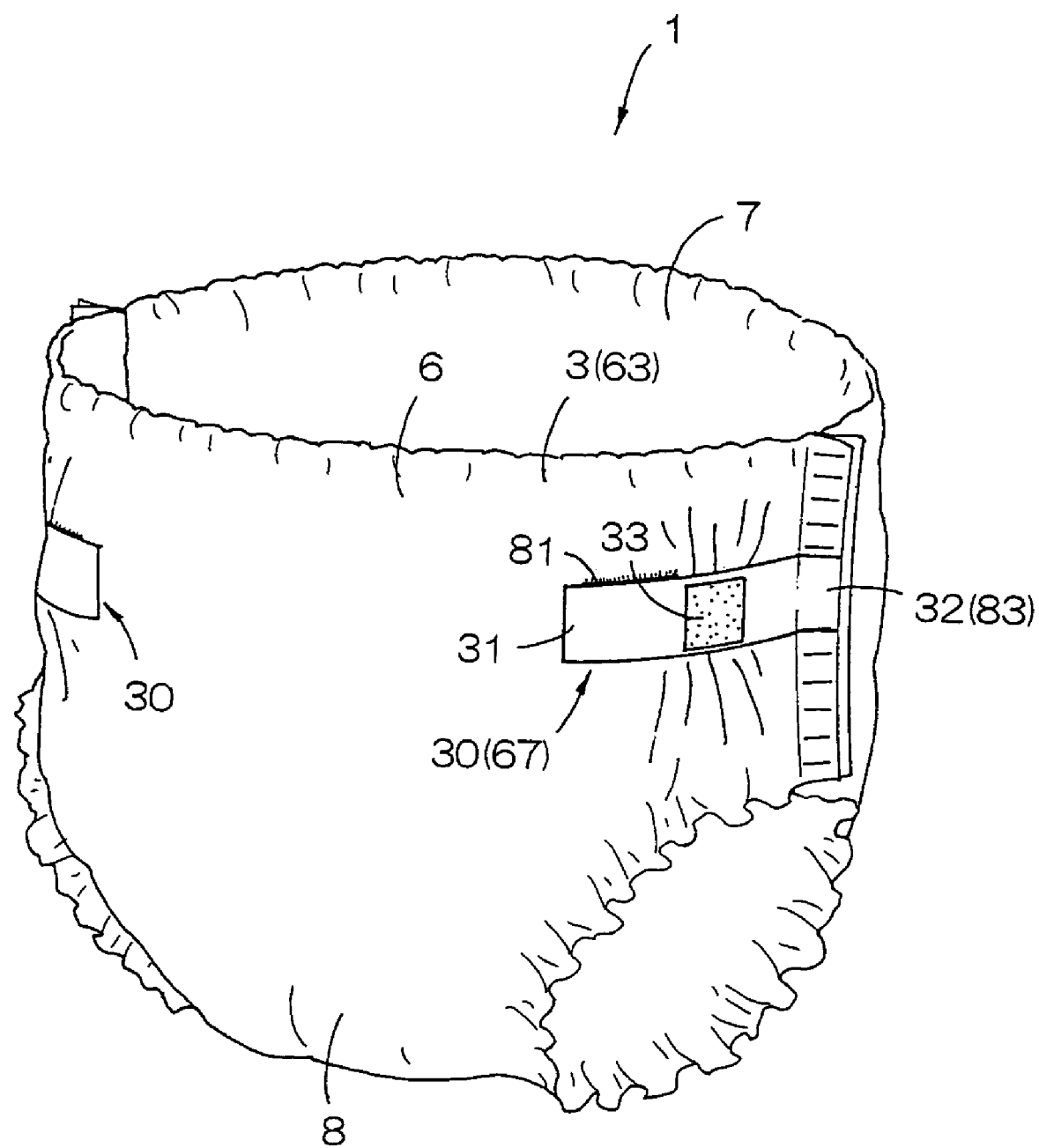
FIG. 13 illustrates a manner of utilizing the tape fasteners depicted in FIG. 12.

FIG. 13 shows an example of a manner to use the tape fastener 30 depicted in FIG. 12. The tape fasteners 30 are attached to each side of the front waist region 6 of the diaper 1. The top tape section 31 of the tape fastener 30 is pulled toward the transversely middle section of the diaper 1, i.e. in the direction indicated by the arrow R in FIG. 12. If a slack is left after the diaper 1 is put on the wearer, the tape fastener 30 may be adjustably pulled in the direction R to tighten the diaper 1 around the waist of the wearer and thereby to provide an appropriate fitness of the diaper 1 to the wearer's waist. If the tape fastener 30 is elastically stretchable in its longitudinal direction, the tape fastener 30 will tighten the diaper 1 around the waist of the wearer in more effective manner. The tape fastener 30 to be used in accordance with the present invention includes such a tape fastener 30 as depicted and used in FIGS. 12 and 13 in addition to the tape fastener 30 depicted and used in FIGS. 3A and 3B.

Without departing from the scope of the invention, it is possible to attach the tape fasteners 30 not only to the open-type diaper 1 as illustrated in Figs. but also to the pull on-type diaper. Instead of attaching the tape fasteners 30 to the hourglass-shaped continuous backsheet 3 forming the front waist region 6, the crotch region 8 and the rear waist region 7, it is possible to attach the tape fasteners 30 to any one of separate sheets defining the surfaces of the front waist region 6 and the rear waist region 7 facing the wearer's garment. While the present invention has been exemplarily described and illustrated with respect to the open-type diaper, the present invention is applicable also to the other disposable wearing article such as disposable training pants or disposable pants.

The process according to the invention for continuously making disposable wearing articles is primarily characterized in that the second continuous web comprising the adhesive tape strips is fed in the second machine direction orthogonal to the first machine direction to the first continuous web running in the first machine direction and cut between the upper tool roll and the lower tool roll both rotating at the rotational speed lower than the running speed of the first continuous web. Such a unique procedure not only alleviates abrasion and/or damage possibly occurring in the upper and lower tool rolls but also stabilizes the position at which the composite of the tape fasteners having been obtained by cutting the second continuous web is supported on the lower tool roll. The process according to the invention is also characterized in that the first continuous web comprising the wearing articles still contiguous to one another is cut so as to bisect the composites attached to this web, respectively, to obtain the individual wearing articles and at the same time to obtain the individual tape fasteners from the respective composites. This unique procedure allows time and labor required for preparation and attachment of these tape fasteners to be reduced in comparison with the case in which the individual tape fasteners are prepared and attached to the wearing article. The position of the first continuous web in the longitudinal direction (i.e., the first cross direction) can be reliably stabilized by feeding the second continuous web by the lower tool roll rotating at the relatively low rotational speed to the first continuous web in the direction orthogonal to this first continuous web.

What is claimed is:

1. A process for continuously making disposable wearing articles, said article having a longitudinal direction and a transverse direction to define a waist-circumferential direction of said article, said article comprising:

an inner surface facing a wearer's body, an outer surface facing a wearer's garment, and a pair of tape strips each having a longitudinal direction and a transverse direction and attached to said outer surface of said article at side edge portions thereof opposed to each other, respectively, so that said longitudinal direction of said tape strip is in conformity with said transverse direction of said article, one of said tape strips being folded in a generally Z-shape while the other of said tape strips being folded in a generally inverted Z-shape, said pair of said tape strips comprising a top tape section, a bottom tape section and an intermediate tape section connecting said top tape section to said bottom tape section, so as to define said Z- or inverted Z-shape, said bottom tape section being configured to be unreleasably attached to said outer surface of said article and provided on a lower surface of said bottom tape section with an adhesive zone, said top tape section being configured to be releasably attached to said outer surface of said article and provided on a lower surface of said top section with a releasably attaching zone and each of the tape strips being attached to said outer surface of said article at said adhesive zone, said process for continuously making the said articles comprising:

continuously feeding a first web in a first machine direction;

continuously feeding, in a second machine direction orthogonal to the first machine direction, a second continuous web of a tape so as to have a vertically depressed Ω-shape;

introducing said second continuous web between an upper tool roll rotating about an axis essentially parallel to the first machine direction and a lower parallel tool roll so that an upper surface of said second continuous web is kept in contact with a peripheral surface of said lower tool roll;

cutting said second web periodically to obtain tape strips that are intermittently spaced in a circumferential direction of said lower tool roll;

compressively squeezing lower surfaces of each of the tape strips between said lower tool roll and a pressure application arrangement configured to periodically move toward said lower tool roll and bring the lower surfaces of said tape strips into adhesive connective contact with an outer surface the first web; and cutting said first web together with said tape strips in a first cross direction orthogonal to said first machine direction so that each tape strip is generally bisected, and to obtain individual sheet members provided with said pair of tape strips one of which is folded in said Z-shape and the other is folded in said inverted Z-shape.

2. The process according to claim 1, wherein said article is a disposable diaper, disposable training pants or disposable pants, said sheet member is configured to be said outer surface of said article in a front or rear waist region and said first web comprises a plurality of said sheet members connected to one another at side edges thereof in said front or rear waist region.

3. The process according to claim 1, wherein said lower tool roll is adapted to rotate in said second machine direction at a constant rotational speed and a ratio between said rotational speed per minute of said lower tool roll and a running speed per minute of said first web in said first machine direction is in a range of 1:2 to 1:40.

4. The process according to claim 1, wherein said pressure application arrangement comprise a pair of hammer rolls extending parallel to each other and adapted to rotate in said first machine direction.

5. The process according to claim 1, wherein the releasably attaching zone includes an adhesive agent coated on said tape strip to be releasably attached to a predetermined portion of said outer surface.

6. The process according to claim 1, wherein the releasably attaching zone includes a hook member provided on said tape strip to be releasably attached to a predetermined portion of said outer surface.

7. The process according to claim 1, wherein said intermediate tape section is releasably attached to said releasably attaching zone of said the top tape section of said tape strip folded in said Z- or inverted Z-shape.

8. The process according to claim 6, wherein at least said intermediate tape section among said top tape section, said bottom tape section and said middle tape section is made of a nonwoven fabric which is releasably engageable with a hook member of a mechanical fastener provided on said top tape section.

9. The process according to claim 1 wherein cutting elements are provided on the upper tool roll for cutting the second web periodically.

10. The process according to claim 1, wherein the lower tool roll comprises a plurality of vacuum holes and the process further comprises:
supplying a first level of vacuum to the holes as they pass over a first zone, and
supplying a second level of vacuum as the holes pass over a second zone.

11. The process according to claim 10, wherein the first and second zones are contiguous, wherein the first zone is located proximate an area between a first location where the second continuous web of tape first contacts the lower tool roll and a second position past the first location at which the composite is cut, and wherein the second zone is configured to hold the cut tape strips on the exterior of the lower tool roll from the second position as they roll down toward a third position proximate the first web.

12. The process according to claim 10, wherein the vacuum in the second zone is higher than the vacuum in the first zone.

* * * * *